United States Patent [19]

Papenfuhs et al.

[11] Patent Number: 5,463,148
[45] Date of Patent: Oct. 31, 1995

[54] PROCESS FOR THE PREPARATION OF CHLOROFLUORONITROBENZENES

[75] Inventors: Theodor Papenfuhs, Frankfurt am Main; Andreas Kanschik-Conradsen, Gernsheim/Rhein; Wilfried Pressler, Kelkheim (Taunus), all of Germany

[73] Assignee: Hoechst Aktiengesellschaft, Frankfurt, Germany

[21] Appl. No.: 238,582

[22] Filed: May 5, 1994

Related U.S. Application Data

[63] Continuation of Ser. No. 914,296, Jul. 15, 1992, abandoned.

[30] Foreign Application Priority Data

Jul. 17, 1991 [DE] Germany .......................... 41 23 600.9

[51] Int. Cl.⁶ .................................................. C07C 205/00
[52] U.S. Cl. .................................... 568/938; 568/937
[58] Field of Search ................................ 568/938, 937; 570/147

[56] References Cited

U.S. PATENT DOCUMENTS

| | | | |
|---|---|---|---|
| 4,069,262 | 1/1978 | Kunz | 568/937 |
| 4,140,719 | 2/1979 | Tull et al. | 568/9 X |
| 4,164,517 | 8/1979 | Fuller | 568/938 |
| 4,226,811 | 10/1980 | Oeser et al. | 568/937 |
| 4,287,374 | 9/1981 | North | 568/937 |
| 4,642,399 | 2/1987 | White | 568/937 X |
| 4,849,552 | 7/1989 | Cantrell | 568/937 |
| 4,973,772 | 11/1990 | Cantrell | 568/937 |
| 4,978,769 | 12/1990 | Kysela et al. | 568/937 X |
| 5,081,288 | 1/1992 | Blank et al. | 570/147 |

FOREIGN PATENT DOCUMENTS

| | | |
|---|---|---|
| 2938939 | 10/1989 | Germany . |
| 1-168645 | 7/1989 | Japan . |
| 2042507 | 9/1980 | United Kingdom . |
| 2058067 | 4/1981 | United Kingdom . |

OTHER PUBLICATIONS

Chen, W., *Chem. Abs.* 113:152000q (1990).

*Primary Examiner*—Shean Wu
*Attorney, Agent, or Firm*—Connolly & Hutz

[57] ABSTRACT

A process for the preparation of chlorofluoronitrobenzenes in high yields, by reacting dichloronitrobenzenes with alkali metal fluorides having a water content of up to about 2.5% by weight in the presence of a quaternary ammonium and/or phosphonium salt, a crown ether and/or polyethylene glycol dimethyl ether as catalyst in the presence of an aprotic solvent, the boiling point of which is below the reaction temperature under the pressure conditions chosen, at temperatures of about 125° to about 200° C.

13 Claims, No Drawings

PROCESS FOR THE PREPARATION OF CHLOROFLUORONITROBENZENES

This is a continuation of application Ser. No. 07/914,296, filed on Jul. 15, 1992 now abandoned.

The present invention relates to an improved process for the preparation of chlorofluoronitrobenzenes in high yields by reaction of dichloronitrobenzenes with alkali metal fluorides in the presence of a catalyst and a small quantity of a solvent, the boiling point of which is below the reaction temperature under the pressure conditions chosen. Chlorofluoronitrobenzenes are important intermediates for the preparation of pharmaceuticals and crop protection agents.

In U.S. Pat. No. 4,164,517, the reaction of 3,4- and 2,4-dichloronitrobenzenes with predried potassium fluoride in dipolar aprotic solvents at temperatures above 200° C. is disclosed. In this case, the yield can be increased with an increasing proportion of the solvent. The procedure is such that when the reaction of 2,4-dichloronitrobenzene is carried out without solvent, only 20% has reacted even after a reaction time of 30 hours at 240° C.

In German patent 29 38 939, a process is disclosed for the preparation of monofluoronitrobenzenes from in particular monochloronitrobenzenes with finely powdered potassium fluoride in the melt and preferably at 140° to 150° C. with addition of tetraalkylammonium salts or arylalkylammonium salts as catalyst. In this case, the reaction times according to the examples are 24 to 28 hours. The disadvantages evident in this process are, apart from the poor space-time yield, that the potassium fluoride preferably used has a water content of less than 0.2% by weight, which necessitates a pretreatment of the potassium fluoride.

There was therefore considerable interest in a more industrially expedient process for the preparation of chlorofluorobenzenes.

It has now surprisingly been found that chlorofluoronitrobenzenes can be prepared advantageously in high yields by reacting dichloronitrobenzenes with alkali metal fluorides having a water content of up to about 2.5% by weight in the presence of a quaternary ammonium and/or phosphonium salt, a crown ether and/or polyethylene glycol dimethyl ether as catalyst in the presence of an aprotic solvent, the boiling point of which is below the reaction temperature under the pressure conditions chosen, at temperatures of about 125° C. to about 200° C., preferably from about 140° to about 190° C.

The starting compounds preferably used are 3,4-dichloronitrobenzene, 2,3-dichloronitrobenzene or 2,5-dichloronitrobenzene.

The alkali metal fluorides used are preferably potassium fluoride, rubidium fluoride or cesium fluoride or combinations thereof. It is an advantage of the process according to the invention that alkali metal fluorides can be used which can have a water content of up to 2.5% by weight, so that for example technical-grade potassium fluoride can be used without pretreatment.

The catalysts can be quaternary ammonium compounds, in particular tetra-$C_1$–$C_{22}$-alkylammonium halides, such as octadecyltrimethylammonium chloride, distearyldimethylammonium chloride, tetramethylammonium chloride, tetramethylammonium chloride, hexadecyltrimethylammonium chloride, benzyltrimethylammonium bromide; tetraarylammonium halides, where the aryl radicals can be for example phenyl or naphthyl radicals, which can be substituted by halogen atoms, branched or unbranched alkyl, nitro, cyano, amino and/or alkoxy groups; or mixed alkylarylammonium halides; in addition quaternary phosphonium compounds, in particular tetra-$C_1$–$C_{22}$-alkylphosphonium halides, such as stearyltributylphosphonium bromide, hexadecyltriethylphosphonium bromide, hexadecyltributylphosphonium bromide; tetraarylphosphonium halides, where the aryl radicals can be for example phenyl or naphthyl radicals, which can be substituted by halogen atoms, branched or unbranched alkyl, nitro, cyano and/or alkoxy groups, or mixed alkylaryl phosphonium halides or crown ethers (see Angewandte Chemie 84 (1972), 16–26, and Römpp's Chemielexikon [Chemical Lexicon], 8th edition (1983)), such as 18-crown-6, polyethylene glycol dimethyl ether and combinations thereof can be used in catalytic quantities.

The abovementioned catalysts are used in the process according to the invention in amounts of about 1 to about 10% by weight, preferably from about 2 to about 5% by weight, relative to dichloronitrobenzene.

As far as the quantitative ratio of dichloronitrobenzene to alkali metal fluoride is concerned, about 1.05 to about 1.7 mol of dichloronitrobenzene are expediently reacted with 1 mol of alkali metal fluoride. However, the dichloronitrobenzene can also be used in a molar excess up to 5:1. By use of the dichloronitrobenzene in excess, the yield of chlorofluoronitrobenzene can be substantially increased.

As far as the aprotic solvents are concerned, the process according to the invention enables solvents of the type mentioned to be used which have a boiling point under the chosen pressure conditions below the reaction temperature, so that they can be continuously distilled off during the reaction. This has the advantage that compounds present in the reaction mixture and also compounds formed during the reaction with boiling points below the reaction temperature are removed with the solvent from the reaction vessel and can be condensed outside the reaction vessel, which leads to a reduced pollution of the exhaust air. Suitable aprotic solvents are for example dimethyl sulfoxide, dimethylacetamide, dimethylformamide, but in particular xylene, o-dichlorobenzene or 2-chlorotoluene.

The process can be carried out at atmospheric pressure and also at overpressure or underpressure. This has the consequence that for example at Underpressure those aprotic solvents can advantageously also be used which boil above the reaction temperature at atmospheric pressure, and at overpressure those aprotic solvents can advantageously also be used which boil relatively far below the reaction temperature at atmospheric pressure.

The aprotic solvents are used in the process according to the invention in only relatively small amounts. It is expedient to use the solvent in an amount of about 2 to about 15 mol %, relative to the dichloronitrobenzene used.

In the process according to the invention it is important that good mixing of the reaction suspension is ensured during the entire reaction.

The examples below serve to illustrate the invention without restricting it thereto.

EXAMPLE 1

100 g of octadecyltrimethylammonium chloride are dissolved at 60° C. in 2900 g (15.1 mol) of 3,4-dichloronitrobenzene. 100 g of 2-chlorotoluene are added to the solution. After addition of 825 g (14.2 mol) of potassium fluoride, the resulting suspension is heated for 11 hours at 180° C. During this time, some of the 2-chlorotoluene is continuously distilled off. The reaction suspension is then quickly filtered off using suction, the filter cake is washed with 2-chlorotoluene and the combined filtrates are fractionated in vacuo. In this manner 1966 g (79% of theory) of 3-chloro-4-fluoronitrobenzene and 340 g of unreacted 3,4-dichloronitrobenzene are obtained.

EXAMPLE 2

70 g of octadecyltrimethylammonium chloride are dissolved at 70° C. in 2020 g (10.5 mol) of 3,4-dichloronitrobenzene and 100 g of o-dichlorobenzene. After addition of 580 g (10 mol) of potassium fluoride, the resulting suspension is heated for 11 hours at 180° C. with stirring and under nitrogen. During this time, some of the o-dichlorobenzene is continuously distilled off. The reaction suspension is then quickly filtered off using suction, the filter cake is washed with o-dichlorobenzene and the combined filtrates are fractionated in vacuo. In this manner 1349 g (77% of theory) of 3-chloro-4-fluoronitrobenzene and 246 g of unreacted 3,4-dichloronitrobenzene are obtained.

EXAMPLE 3

20 g of tetramethylammonium chloride are dissolved at 70° C. in 100 g of 2-chlorotoluene. 1230 g (6.5 mol) of 2,3-dichloronitrobenzene are added to the solution. After addition of 290 g (5 mol) of potassium fluoride, the resulting suspension is heated for 14 hours at 180° C. with stirring and under nitrogen. During this time, some of the 2-chlorotoluene is continuously distilled off. The reaction suspension is then quickly filtered off using suction, the filter cake is washed with 2-chlorotoluene and the combined filtrates are fractionated in vacuo. In this manner 505 g (57% of theory) of 2-fluoro-3-chloronitrobenzene and 437 g of unreacted 2,3-dichloronitrobenzene are obtained.

EXAMPLE 4

25 g of hexadecyltributylphosphonium bromide are dissolved at 60° C. in 1010 g (5.25 mol) of 3,4-dichloronitrobenzene. 100 g of 2-chlorotoluene are added to the solution. After addition of 290 g (5.0 mol) of potassium fluoride, the resulting suspension is heated for 16 h at 200° C. During this time, some of the 2-chlorotoluene is continuously distilled off. The reaction suspension is then quickly filtered off using suction, the filter cake is washed with 2-chlorotoluene and the combined filtrates are fractionated in vacuo. In this manner, 711 g (81% of theory) of 3-chloro-4-fluoronitrobenzene and 115 g of unreacted 3,4-dichloronitrobenzene are obtained.

We claim:

1. A process for the preparation of chlorofluoronitrobenzenes in high yields, which comprises the steps of:

reacting dichloronitrobenzenes with alkali metal fluorides having a water content of from 0.2% by weight up to about 2.5% by weight in the presence of a catalyst selected from the group consisting of a quaternary ammonium salt, a quaternary phosphonium salt, a crown ether, a polyethylene glycol dimethyl ether, and mixtures thereof in the presence of an aprotic solvent, the boiling point of said aprotic solvent being below the reaction temperature under the pressure conditions chosen, at temperatures of about 125° C. to about 200° C., and removing compounds from the reaction by removing the boiling solvent during the reaction.

2. The process as claimed in claim 1, wherein the reaction is carried out at temperatures of about 140° to about 190° C.

3. The process as claimed in claim 1, wherein the quaternary ammonium salts are selected from the group consisting of tetra-$C_1$–$C_{22}$-alkylammonium halides, tetraarylammonium halides, mixed alkylarylammonium halides, and mixtures thereof the quaternary phosphonium salts are selected from the group consisting of tetra-$C_1$–$C_{22}$-alkylphosphonium halides, tetraarylphosphonium halides, mixed alkylarylphosphonium halides, and mixtures thereof and the crown ether used is 18-crown-6.

4. The process as claimed in claim 1, wherein the catalyst used is selected from the group consisting of octadecyltrimethylammonium chloride, distearyldimethylammonium chloride, tetramethylammonium chloride, tetramethylammonium bromide, hexadecyltrimethylammonium chloride, benzyltrimethylammonium bromide, stearyltributylphosphonium bromide, hexadecyltriethylphosphonium bromide, hexadecyltributylphosphonium bromide, and mixtures thereof.

5. The process as claimed in claim 1, wherein the catalyst is used in amounts of about 2 to about 10% by weight, relative to dichloronitrobenzene.

6. The process as claimed in claim 1, wherein the catalyst is used in amounts of about 2 to about 5% by weight, relative to dichloronitrobenzene.

7. The process as claimed in claim 1, wherein the alkali metal fluoride used is potassium fluoride, rubidium fluoride or cesium fluoride or combinations thereof.

8. The process as claimed in claim 1, wherein about 1.05 to about 1.7 mol of dichloronitrobenzene are reacted with 1 mol of alkali metal fluoride.

9. The process as claimed in claim 1, wherein about 1.05 to about 5 mol of dichloronitrobenzene are reacted with 1 mol of alkali metal fluoride.

10. The process as claimed in claim 1, wherein the aprotic solvent used is xylene, o-dichlorobenzene, 2-chlorotoluene, dimethyl sulfoxide, dimethylacetamide or dimethylformamide.

11. The process as claimed in claim 1, wherein about 2 to about 15 mol % of aprotic solvent are used, relative to the dichloronitrobenzene used.

12. The process as claimed in claim 1, wherein mixing of the reaction suspension is carried out during the entire reaction.

13. The process as claimed in claim 1, wherein atmospheric pressure, overpressure or underpressure is employed.

\* \* \* \* \*